United States Patent
Ballard et al.

(10) Patent No.: US 11,426,223 B2
(45) Date of Patent: *Aug. 30, 2022

(54) BONE SCREW AND METHOD OF MANUFACTURE

(71) Applicant: Warsaw Orthopedic, Inc., Warsaw, IN (US)

(72) Inventors: Rodney Ray Ballard, Lakeland, TN (US); William Alan Rezach, Covington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/282,388

(22) Filed: Feb. 22, 2019

(65) Prior Publication Data

US 2020/0268425 A1 Aug. 27, 2020

(51) Int. Cl.
| | |
|---|---|
| *A61B 17/86* | (2006.01) |
| *A61F 2/28* | (2006.01) |
| *A61F 2/44* | (2006.01) |
| *A61F 2/46* | (2006.01) |
| *A61F 2/30* | (2006.01) |
| *A61L 27/36* | (2006.01) |

(52) U.S. Cl.
CPC ............. *A61B 17/866* (2013.01); *A61F 2/28* (2013.01); *A61F 2/30771* (2013.01); *A61F 2/44* (2013.01); *A61F 2/4611* (2013.01); *A61B 17/8605* (2013.01); *A61F 2002/2835* (2013.01); *A61F 2310/00023* (2013.01); *A61L 27/3608* (2013.01); *A61L 2430/02* (2013.01)

(58) Field of Classification Search
CPC ............ A61B 17/7032; A61B 17/7034; A61B 17/866; A61F 2/30771
USPC .................................................. 606/246–279
See application file for complete search history.

(56) References Cited

U.S. PATENT DOCUMENTS

| | | |
|---|---|---|
| 7,850,717 B2 | 12/2010 | Dewey et al. |
| 2008/0177331 A1 | 7/2008 | Perez-Cruet et al. |
| 2010/0042167 A1 | 2/2010 | Nedosky et al. |
| 2011/0172798 A1 | 7/2011 | Staiger et al. |
| 2015/0018956 A1 | 1/2015 | Steinmann et al. |
| 2015/0032159 A1 | 1/2015 | Beger et al. |
| 2015/0223907 A1 | 8/2015 | Kieser |
| 2015/0313658 A1* | 11/2015 | Kolb ................. A61B 17/8625 606/309 |
| 2016/0157908 A1* | 6/2016 | Cawley ................. A61F 2/0077 606/301 |
| 2016/0367371 A1 | 12/2016 | de Beaubien et al. |
| 2017/0165077 A1 | 6/2017 | McDonnell |
| 2017/0245851 A1 | 8/2017 | Biedermann et al. |
| 2018/0028242 A1 | 2/2018 | Parekh et al. |

(Continued)

*Primary Examiner* — Si Ming Ku
(74) *Attorney, Agent, or Firm* — Sorell, Lenna & Schmidt, LLP

(57) ABSTRACT

An implant receiver comprises a body formed by a first manufacturing method, the body including an outer surface and having spaced apart walls defining a cavity configured for disposal of a spinal implant; and at least one layer being formed onto at least a portion of the outer surface by a second manufacturing method. In some embodiments, systems, spinal constructs, surgical instruments and methods are disclosed. In some embodiments, systems, spinal constructs, surgical instruments and methods are disclosed.

20 Claims, 3 Drawing Sheets

(56) References Cited

U.S. PATENT DOCUMENTS

2018/0042702 A1    2/2018  Stuebinger
2019/0008562 A1*  1/2019  Melton .................. B33Y 50/02
2019/0239935 A1*  8/2019  Willis .................. A61B 17/866

* cited by examiner

BONE SCREW AND METHOD OF MANUFACTURE

TECHNICAL FIELD

The present disclosure generally relates to medical devices for the treatment of spinal disorders, and more particularly to a spinal implant system having a variable structured spinal implant that can be manufactured by a method including one or a plurality of manufacturing techniques.

BACKGROUND

Spinal pathologies and disorders such as kyphosis, scoliosis and other curvature abnormalities, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including bone fasteners are often used to provide stability to a treated region. Such bone fasteners are traditionally manufactured using a medical machining technique. This disclosure describes an improvement over these prior technologies.

SUMMARY

In one embodiment, an implant receiver is provided. The implant receiver comprises a body formed by a first manufacturing method. The body includes an outer surface and has spaced apart walls that define a cavity configured for disposal of a spinal implant. At least one layer is formed onto at least a portion of the outer surface by a second manufacturing method. In some embodiments, systems, spinal constructs, surgical instruments and methods are disclosed.

In one embodiment, a method for fabricating an implant receiver is provided. The method comprises the steps of: forming a body of an implant receiver by a first manufacturing method, the body including an outer surface and spaced apart walls that define a cavity configured for disposal of a spinal implant; forming at least one layer onto at least a portion of the outer surface by a second manufacturing method including an additive manufacturing method wherein a processor instructs an additive manufacturing apparatus to form the at least one layer.

In one embodiment, a bone screw is provided. The bone screw comprises a shaft including at least one thread having an external thread form. An implant receiver is formed by a first manufacturing method. The receiver includes spaced apart walls defining a U-shaped cavity configured for disposal of a spinal implant and an outer surface. A layer is formed onto at least a portion of the outer surface by a second manufacturing method.

BRIEF DESCRIPTION OF THE DRAWINGS

The present disclosure will become more readily apparent from the specific description accompanied by the following drawings, in which.

DETAILED DESCRIPTION

Figure 1:
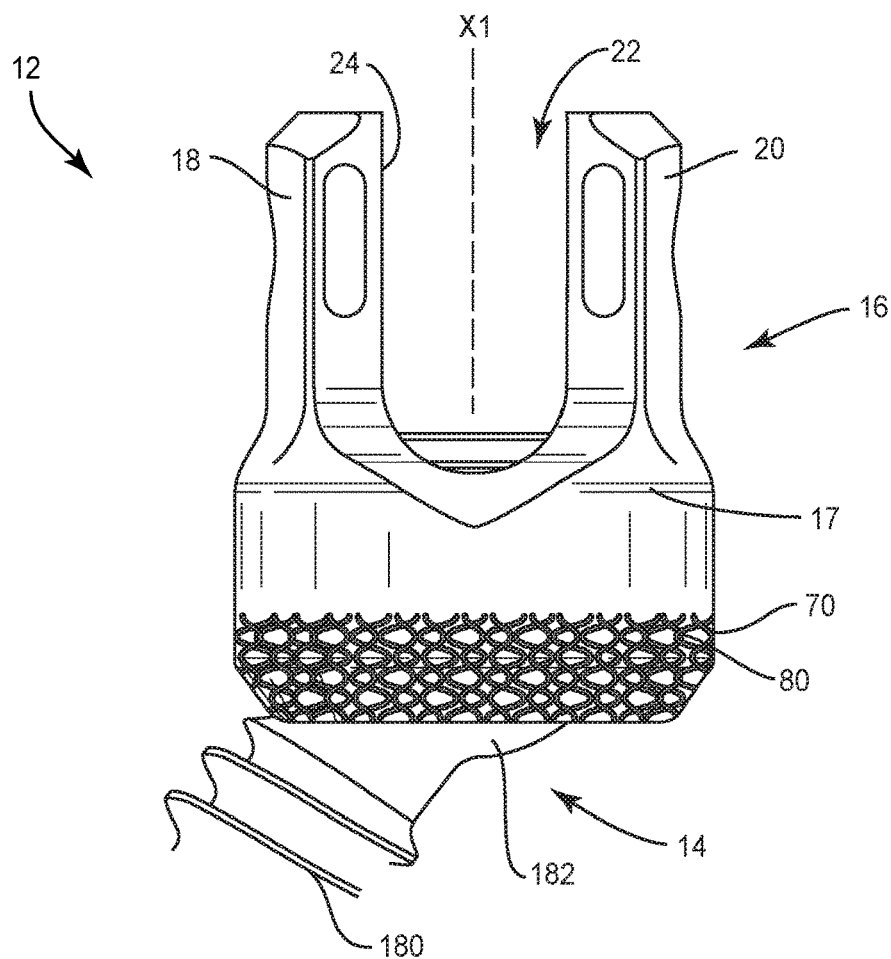
FIG. 1 is a side view of components of one embodiment of a system in accordance with the principles of the present disclosure.
Figure 4:
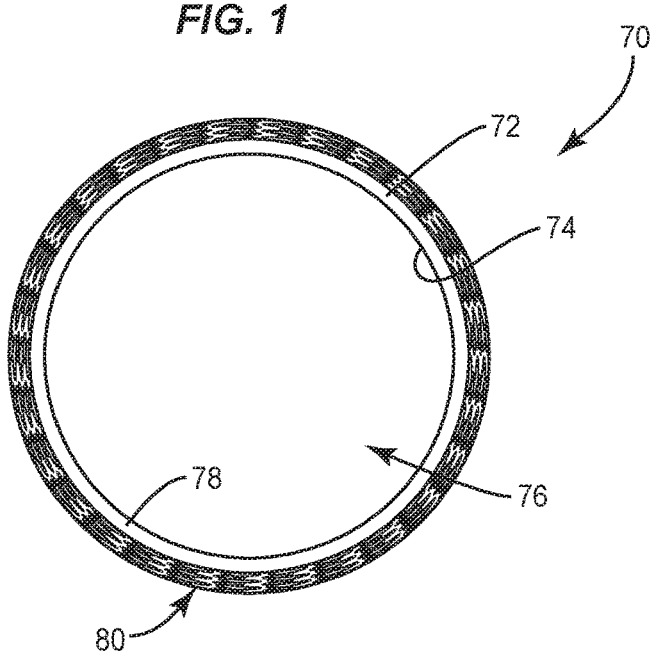
FIG. 4 is a cross section view of one embodiment of a system in accordance with the principles of the present disclosure.

The exemplary embodiments of a surgical system and related methods of use disclosed are discussed in terms of medical devices for the treatment of musculoskeletal disorders and more particularly, in terms of a variable structured spinal implant. In some embodiments, the spinal implant system includes a spinal implant comprising a variable structured implant receiver.

In some embodiments, the spinal implant system of the present disclosure comprises a spinal implant, such as, for example, an implant receiver that is manufactured by combining traditional manufacturing methods and additive manufacturing methods. In some embodiments, a layer is applied by additive manufacturing in areas where the implant receiver can benefit from materials, surface texture, and/or other properties that can be associated with using additive manufacturing.

In some embodiments, the implant receiver includes a hybrid configuration that combines a manufacturing method, such as, for example, one or more traditional manufacturing features and materials and a manufacturing method, such as, for example, one or more additive manufacturing features and materials. In some embodiments, the spinal implant system of the present disclosure comprises an implant receiver that promotes bony in-growth by adding a layer thereto by additive manufacturing. In some embodiments, the implant receiver includes a variable structure, such as, for example, any combination of solid, roughened surfaces, porous surfaces, honeycomb filled, structure having a trabecular configuration, or other porous or roughened configurations. In some embodiments, the implant receiver of the present disclosure aids in the promotion of bony fusion. In some embodiments, the porous layer is disposed about all or only a portion of a base, for example, disposed about an outer diameter of the base. In some embodiments, this configuration optimizes bony in-growth with the screw head of a pedicle screw to promote fusion. In some embodiments, this configuration resists and/or prevents toggle. In some embodiments, the spinal implant system of the present disclosure comprises a modular screw system including screw shaft assemblies and implant receiver/head assemblies that may be joined together during manufacturing or intra-operatively, such as, for example, during a surgical procedure in an operating room.

In some embodiment, the implant receiver includes a porous or surface textured layer at a bone interface portion of the implant receiver. In some embodiments, the porous layer is configured to enhance the implant-bone interface. In some embodiments, the porous layer is applied by an additive manufacturing and other components of the bone screw are manufactured by a traditional manufacturing method. In some embodiments, the variable structure bone screw provides for the mechanical strength of the bone screw and the added porous layer enhances the implant-bone interface.

In some embodiments, additive manufacturing includes 3-D printing. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing and on-demand manufacturing. In some embodiments, the spinal implant system comprises one or more components, as described herein, of a spinal implant being manufactured by a fully additive process and grown or otherwise printed. In some embodiments, the implant receiver and/or head assembly of the present disclosure includes a non-solid portion, for example, a porous layer that is applied to a base of the implant receiver and/or head assembly via additive manufacturing, for example, 3-D printing. In some embodiments, this configuration avoids compromising the integrity of a spinal construct and promotes bone fusion.

In some embodiments, the spinal implants, surgical instruments and/or medical devices of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the spinal implants, surgical instruments and/or medical devices of the present disclosure may be employed with other osteal and bone related applications, including those associated with diagnostics and therapeutics. In some embodiments, the spinal implants, surgical instruments and/or medical devices of the present disclosure may be alternatively employed in a surgical treatment with a patient in a prone or supine position, and/or employ various surgical approaches to the spine, including anterior, posterior, posterior mid-line, lateral, postero-lateral, and/or anterolateral approaches, and in other body regions such as maxillofacial and extremities. The spinal implants, surgical instruments and/or medical devices of the present disclosure may also be alternatively employed with procedures for treating the lumbar, cervical, thoracic, sacral and pelvic regions of a spinal column. The spinal implants, surgical instruments and/or medical devices of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a spinal implant, a method of manufacturing a spinal implant, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-5, there are illustrated components of a spinal implant system 10 including spinal implants, surgical instruments and medical devices.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant comprising a bone fastener, such as, for example, a bone screw 12. Bone screw 12 includes an implant receiver and/or head assembly having a variably structured configuration that facilitates bone growth through bone screw 12 and/or fixation of bone screw 12 with tissue. Bone screw 12 comprises a screw shaft 14 and an implant receiver 16. Receiver 16 includes a body 17 that defines an implant cavity 22 and a base 70. Base 70 includes a layer 80 applied by an additive manufacturing process.

In various embodiments, body 17 has an even, uninterrupted edge surface. Body 17 may also include an even, solid surface relative layer 80, as described herein, which provides a variable configuration bone screw 12.

In some embodiments, body 17 is fabricated by a first manufacturing method. The manufacturing method can include a traditional machining method, subtractive, deformative or transformative manufacturing methods. In some embodiments, the traditional manufacturing method may include cutting, grinding, rolling, forming, molding, casting, forging, extruding, whirling, grinding and/or cold working. In some embodiments, the traditional manufacturing method includes components being formed by a medical machining process. In some embodiments, medical machining processes can include use of computer numerical control (CNC) high speed milling machines, Swiss machining devices, CNC turning with living tooling and/or wire EDM 4th axis. In some embodiments, the manufacturing method includes a finishing process, such as, for example, laser marking, tumble blasting, bead blasting, micro blasting and/or powder blasting.

In some embodiments, body 17 includes a pair of spaced apart arms 18, 20. Arms 18, 20 define implant cavity 22 therebetween. Implant cavity 22 is configured for disposal of a component of a spinal construct, such as, for example, a spinal rod (not shown). In various embodiments, arms 18, 20 each extend generally parallel to an axis X1. In some embodiments, arm 18 and/or arm 20 may be disposed at alternate orientations, relative to axis X1. For example, arm 18 and/or arm 20 may be disposed transverse, perpendicular and/or other angular orientations, such as acute or obtuse, coaxial and/or may be offset or staggered relative to axis X1. Arms 18, 20 each include an outer surface, which may be arcuate, extending between a pair of side edges or surfaces.

In various embodiments, at least one of the outer surfaces and the side surfaces of arms 18, 20 have at least one recess or cavity therein configured to receive an insertion tool, compression instrument, and/or instruments for inserting and tensioning bone screw 12. In some embodiments, arms 18, 20 are connected at proximal and distal ends thereof such that receiver 16 defines a closed spinal rod slot.

Cavity 22 may be substantially U-shaped. In some embodiments, all or only a portion of cavity 22 has alternate cross section configurations, such as, for example, closed, V-shaped, W-shaped, oval, oblong triangular, square, polygonal, irregular, uniform, non-uniform, offset, staggered, and/or tapered.

Receiver 16 includes an inner surface 24. In various embodiments, portion of surface 24 includes a thread form located adjacent arm 18 and adjacent arm 20. The thread form is configured for engagement with a coupling member, such as, for example, a setscrew (not shown), to retain the spinal rod within cavity 22. In some embodiments, surface 24 may be disposed with the coupling member in alternate fixation configurations, such as, for example, friction fit, pressure fit, locking protrusion/recess, locking keyway and/or adhesive. In some embodiments, all or only a portion of surface 24 may have alternate surface configurations to enhance engagement with the spinal rod and/or the setscrew, such as, for example, rough, arcuate, undulating, mesh, porous, semi-porous, dimpled and/or textured. In some embodiments, receiver 16 may include alternate configurations, such as, for example, closed, open and/or side access.

In some embodiments, receiver 16 includes a surface configured for disposal of a part, such as, for example, a crown (not shown). The crown is configured for disposal within implant cavity 22. In some embodiments, the crown includes a curved portion configured for engagement with the spinal rod.

Base 70 includes porous layer 80 to enhance fixation and/or facilitate bone growth, as described herein. Layer 80 is applied with a second manufacturing, as described herein. In some embodiments, the manufacturing method can include an additive manufacturing method by disposing a material onto a surface 78 of a wall 72, as described herein. All or a portion of base 70 is configured to interface bone. Layer 80 is provided to increase a base 70-to-bone interface.

Base 70 having layer 80 enhances fixation and/or facilitates bone growth, as described herein. In some embodiments, tissue becomes imbedded with layer 80 to promote bone growth, enhance fusion of bone screw 12 with vertebral tissue, and/or prevent toggle of bone screw 12 in one or multiple motion planes.

Body 17 is in various embodiments manufactured by a traditional manufacturing process (not including additive manufacturing, for instance), and layer 80 is applied to surface 78 by an additive manufacturing process. Having body 17 and the other components of bone screw 12 manufactured by traditional manufacturing processes maintains the mechanical performance characteristics of bone screw 12, while also enhancing bone growth and fusion.

Base 70 of receiver 16 includes wall 72. Wall 72 includes an inner surface 74 that defines a cavity 76, and outer surface 78. Cavity 76 is configured for disposal of a head 182 of screw shaft 14. In various embodiments, wall 72 includes an even, uninterrupted configuration and includes an even, solid surface 78 relative to the surface of layer 80. Surface 78 is configured for providing a fabrication platform for forming layer 80 thereon using a second manufacturing method such as, for example, an additive manufacturing method, as described herein. In some embodiments, an overall width of wall 72 including layer 80 (e.g., outside diameter, or maximum width) is the same as a width of a traditional receiver. In some embodiments, receiver 16 has a solid configuration relative to the layer 80. In some embodiments, receiver 16 is connectable with a bone screw shaft.

Figure 2:
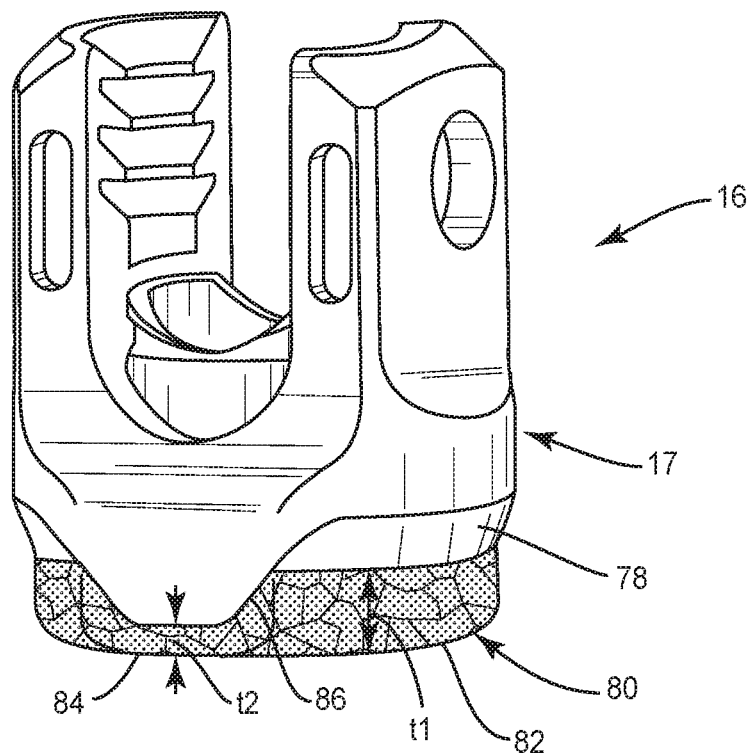
FIG. 2 is a perspective view of components of one embodiment of a system in accordance with the principles of the present disclosure.
Figure 3:
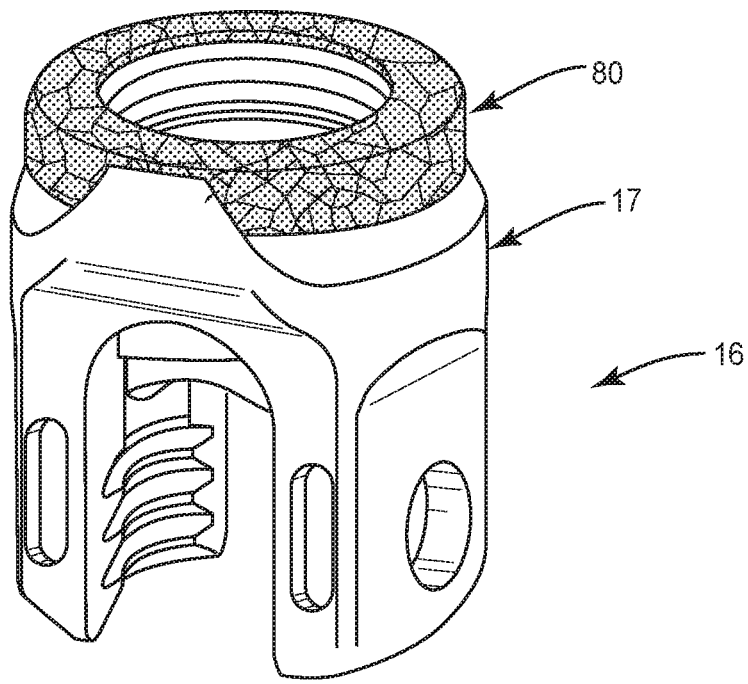
FIG. 3 is a perspective view of one embodiment of a system in accordance with the principles of the present disclosure.

Layer 80 is applied to at least a portion of an outer circumference of surface 78. In some embodiments, layer 80 includes a portion 82 and a portion 84, as shown in FIGS. 2 and 3. Portion 82 includes a first thickness t1 and portion 84 includes a second thickness t2, as shown in FIG. 2. In some embodiments, portion 82 includes a tapered portion 86 that connects portion 82 and portion 84. In some embodiments, layer 80 has various configurations along surface 78, such as, a non-solid configuration, such as, for example, a porous structure and/or a trabecular configuration.

In some embodiments, additive manufacturing includes 3-D printing, as described herein. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing or on-demand manufacturing.

In some embodiments, layer 80 is applied by additive manufacturing, as described herein, and mechanically attached to surface 78 by, for example, welding, threading, adhesives and/or staking. In some embodiments, layer 80 has a porous configuration, a lattice, a trabecular configuration and/or a roughened surface to promote bone growth through the layer. In some embodiments, additive manufacturing includes heating a material in a selective material formation onto a portion of the outer surface of the implant receiver.

In various embodiments, the non-solid configuration provides one or a plurality of pathways to facilitate bone through growth within, and in some embodiments all of the way through, from one surface to an opposite surface of bone screw 12. In some embodiments, one or more portions, layers and/or substrates of layer 80 may be disposed side by side, offset, staggered, stepped, tapered, end to end, spaced apart, in series and/or in parallel. In some embodiments, layer 80 is disposed about an entire outer circumference of receiver 16. In some embodiments, layer 80 disposed about an outer circumference of a lower portion near base 70 of receiver 16, as shown in FIGS. 2 and 3.

In some embodiments, layer 80 defines a thickness, which may be uniform, undulating, tapered, increasing, decreasing, variable, offset, stepped, arcuate, angled and/or staggered. In some embodiments, layer 80 includes one or more layers of a matrix of material. In some embodiments, layer 80 includes one or a plurality of cavities, spaces and/or openings. In some embodiments, layer 80 forms a rasp-like configuration. In some embodiments, layer 80 is configured to engage tissue, such as, for example, cortical bone and/or cancellous bone, such as, to cut, shave, shear, incise and/or disrupt such tissue. In some embodiments, all or a portion of layer 80 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. Layer 80 may be rough, textured, porous, semi-porous, dimpled, knurled, toothed, grooved and/or polished to facilitate engagement and cutting of tissue.

In some embodiments, the non-solid configuration is configured as a lattice extending along surface 78. In some embodiments, the lattice may include one or more portions, layers and/or substrates. Disclosures herein involving a porous, or other particular type of non-solid structure, are meant to disclose at the same time analogous embodiments in which other non-solid structure in addition or instead of the particular type of structure.

In some embodiments, layer 80 is fabricated according to instructions received from a computer and processor based on the digital rendering and/or data of the selected configuration, via the additive manufacturing process. See also, the examples and disclosure of the additive and three-dimensional manufacturing systems and methods shown and described in commonly owned and assigned U.S. patent application Ser. No. 15/889,355, filed Feb. 6, 2018; and the examples and disclosure of the additive and three dimensional manufacturing systems and methods shown and described in commonly owned and assigned U.S. patent application Ser. Nos. 15/666,305 and 15/666,281, filed Aug. 1, 2018; the entire contents of each of these references being hereby incorporated by reference herein in their respective entireties.

In one embodiment, one or more manufacturing methods for fabricating layer 80 and other components of bone screw 12, such as, for example, screw shaft 14 and receiver 16 include imaging patient anatomy with imaging techniques, such as, for example, x-ray, fluoroscopy, computed tomography (CT), magnetic resonance imaging (MRI), surgical navigation, bone density (DEXA) and/or acquirable 2-D or 3-D images of patient anatomy. Selected configuration parameters of screw shaft 14, receiver 16 and layer 80 and/or other components of bone screw 12 are collected, calculated and/or determined. Such configuration parameters can include one or more of patient anatomy imaging, surgical treatment, historical patient data, statistical data, treatment algorithms, implant material, implant dimensions, porosity and/or manufacturing method. In some embodiments, the configuration parameters can include implant material and porosity of layer 80 determined based on patient anatomy and the surgical treatment. In some embodiments, the implant material includes a selected porosity of layer 80, as described herein.

Figure 5:
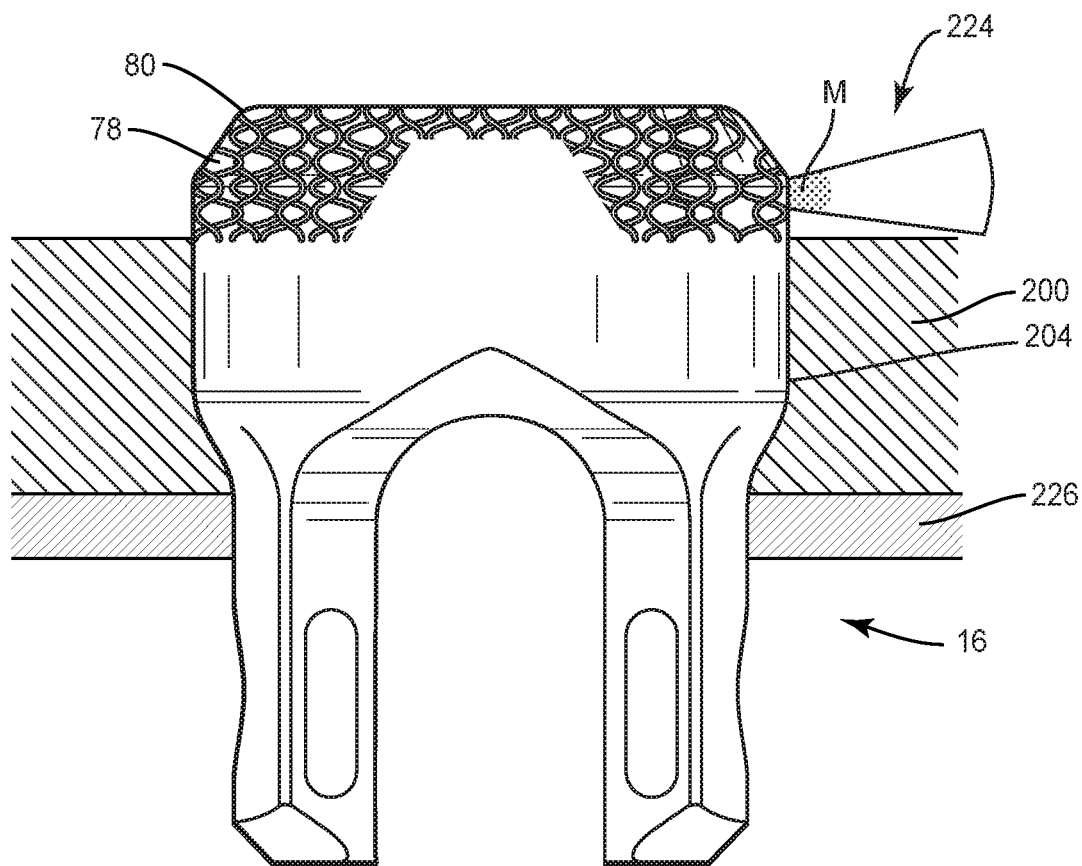
FIG. 5 is a side view, in part cross section, of components of one embodiment of a system in accordance with the principles of the present disclosure.

In some embodiments, the processor can instruct motors (not shown) that control movement and rotation of components, for example, a build plate 200, receiver 16 and/or laser emitting devices, as described herein. In some embodiments, layer 80 is applied by utilizing a radiation source to melt and solidify a material M onto surface 78 into a desired three-dimensional shape based on the selected configuration parameters, as described herein. In some embodiments, the radiation source includes a laser device 224, as shown in FIG. 5, which comprises a carbon dioxide laser. In some embodiments, laser device 224 may include a beam of any wavelength of visible light or UV light. In some embodiments, alternative forms of radiation, such as, for example, microwave, ultrasound or radio frequency radiation are provided. In some embodiments, laser device 224 is configured to be focused on a portion of surface 78 to sinter material M deposited thereon, as shown in FIG. 5. In some embodiments, laser device 224 emits a beam having a diameter between about 0.01 mm and about 0.8 mm. In some embodiments, the diameter of the beam may be between about 0.1 mm and about 0.4 mm. In some embodiments, the diameter of the beam is adjustable to customize the intensity of the sintering.

Build plate 200 includes a surface that defines one or a plurality of openings 204. Each opening 204 is configured for disposal of receiver 16 to orient base 70 as a fabrication platform for forming layer 80 thereon with an additive manufacturing method, as described herein. Surface 78 extends from opening 204 to orient surface 78 for selective laser melting with a powder bed process by the radiation source.

Build plate 200 is mounted with a platform 226 such that build plate 200 can be moved relative to an enclosure in one or more directions to generate layer 80 on surface 78, layer by layer, based on the digital rendering and/or data. In some embodiments, build plate 200 can be translated vertically, horizontally or diagonally, rotated, pivoted, raised and/or lowered to generate the distal portion. In some embodiments, build plate 200 can be moved relative to the enclosure slidably, continuously, incrementally, intermittently, automatically, manually, selectively and/or via computer/processor control. In some embodiments, an apparatus comprising an additive manufacturing device that employs selective laser melting with a powder bed process to create 3D objects is provided. See, for example, the Lasertec 30 SLM additive manufacturing machine manufactured by DMG MORI Co. Ltd. located at 2-35-16 Meieki, Nakamura-ku, Nagoya City 450-0002, Japan.

In some embodiments, the selected configuration parameters of layer 80 and/or other components of bone screw 12 are patient specific. In some embodiments, the selected configuration parameters of layer 80 and/or other components of bone screw 12 are based on generic or standard configurations and/or sizes and not patient specific. In some embodiments, the selected configuration parameters of layer 80 and/or other components of bone screw 12 are based on one or more configurations and/or sizes of components of a kit of spinal implant system 10 and not patient specific.

Screw shaft 14 defines an even, uninterrupted edge surface and includes an even, solid surface relative to the surface of layer 80. Shaft 180 is configured to penetrate tissue, such as, for example, bone. In some embodiments, shaft 180 includes an outer surface having an external thread form. In some embodiments, the external thread form may include a single thread turn or a plurality of discrete threads. Head 182 includes a tool engaging portion configured to engage a surgical tool or instrument, as described herein. In some embodiments, the tool engaging portion includes a hexagonal cross-section to facilitate engagement with a surgical tool or instrument, as described herein. In some embodiments, the tool engaging portion may have alternative cross-sections, such as, for example, rectangular, polygonal, hexalobe, oval, or irregular. In some embodiments, head 182 includes a plurality of ridges to improve purchase of head 182 with the crown. Head 182 is configured for attachment with receiver 16, as described herein.

In some embodiments, the external thread form is fabricated to include a fine, closely-spaced and/or shallow configuration to facilitate and/or enhance engagement with tissue. In some embodiments, the external thread form is fabricated to be continuous along shaft 180. In some embodiments, the external thread form is fabricated to be intermittent, staggered, discontinuous and/or may include a single thread turn or a plurality of discrete threads. In some embodiments, shaft 180 is fabricated to include penetrating elements, such as, for example, a nail configuration, barbs, expanding elements, raised elements, ribs, and/or spikes. In some embodiments, the external thread form is fabricated to be self-tapping or intermittent at a distal tip. In some embodiments, the distal tip may be rounded. In some embodiments, the distal tip may be self-drilling. In some embodiments, the distal tip includes a solid outer surface.

Surface 74 facilitates engagement of head 182 with base 70 via a pressure and/or force fit connection. In some embodiments, surface 74 facilitates a non-instrumented assembly with receiver 16 and head 182 via an expandable ring. In some embodiments, receiver 16 may be disposed with head 182 in alternate fixation configurations, such as, for example, friction fit, pressure fit, locking protrusion/recess, locking keyway and/or adhesive. In some embodiments, receiver 16 is configured for rotation relative to head 182. In some embodiments, receiver 16 is configured for rotation in range of 360 degrees relative to head 182 to facilitate positioning of shaft 180 with tissue. In some embodiments, receiver 16 is configured for selective rotation in range of 360 degrees relative to and about head 182 such that shaft 180 is selectively aligned for rotation in a plane relative to receiver 16.

In some embodiments, receiver 16 is manually engageable with screw shaft 14 in a non-instrumented assembly, as described herein. In some embodiments, manual engagement and/or non-instrumented assembly of receiver 16 and screw shaft 14 includes coupling without use of separate and/or independent instrumentation engaged with screw shaft 14 components to effect assembly. In some embodiments, manual engagement and/or non-instrumented assembly includes a practitioner, surgeon and/or medical staff grasping receiver 16 and screw shaft 14 and forcibly assembling the components. In some embodiments, manual engagement and/or non-instrumented assembly includes a practitioner, surgeon and/or medical staff grasping receiver 16 and screw shaft 14 and forcibly snap fitting the components together, as described herein. In some embodiments, manual engagement and/or non-instrumented assembly includes a practitioner, surgeon and/or medical staff grasping receiver 16 and screw shaft 14 and forcibly pop fitting the components together and/or pop fitting receiver 16 onto screw shaft 14, as described herein. In some embodiments, a force in a range of about 2 to about 50 N is required to manually engage receiver 16 and screw shaft 14 and forcibly assemble the components. For example, a force in a range of about 2 to about 50 N is required to snap fit and/or pop fit assemble receiver 16 and screw shaft 14. In some embodiments, a force in a range of about 5 to about 10 N is required to manually engage receiver 16 and screw shaft 14 and forcibly assemble the components. For example, a force in a range of about 5 to about 10 N is required to snap fit and/or pop fit assemble receiver 16 and screw shaft 14. In some embodiments, screw shaft 14 is manually engaged with base 70 and/or receiver 16 in a non-instrumented assembly, as described herein, such that removal of receiver 16 and screw shaft 14 requires a force and/or a pull-out strength of at least about 5000 N. In some embodiments, this configuration provides manually engageable components that are assembled without instrumentation, and subsequent to assembly, the assembled components have a selected pull-out strength and/or can be pulled apart, removed and/or separated with a minimum required force. In some embodiments, spinal implant system 10 comprises a spinal implant kit, as described herein, which includes a plurality of screw shafts 14 and/or receivers 16.

In some embodiments, bone screw 12 can include various configurations, such as, for example, a posted screw, a pedicle screw, a bolt, a bone screw for a lateral plate, an interbody screw, a uni-axial screw, a fixed angle screw, a multi-axial screw, a side loading screw, a sagittal adjusting screw, a transverse sagittal adjusting screw, an awl tip, a dual rod multi-axial screw, midline lumbar fusion screw and/or a sacral bone screw.

In assembly, operation and use, spinal implant system 10 is employed to treat an affected section of vertebrae. A medical practitioner obtains access to a surgical site including the vertebrae in any appropriate manner, such as through incision and retraction of tissues. The components of spinal implant system 10 including bone screw 12 are employed to augment a surgical treatment. Bone screw 12 can be delivered to a surgical site as a pre-assembled device. In some embodiments, bone screw 12 can be delivered to a surgical site assembled in situ. Spinal implant system 10 may be completely or partially revised, removed or replaced.

Surgical system 10 may be used with surgical methods or techniques including open surgery, mini-open surgery, minimally invasive surgery and percutaneous surgical implantation, whereby the vertebrae is accessed through a mini-incision, or sleeve that provides a protected passageway to the area. Once access to the surgical site is obtained, a surgical treatment, for example, corpectomy and/or discectomy, can be performed for treating a spine disorder.

Bone screw 12 is connected with a surgical instrument, such as, for example, a driver (not shown) and is delivered to the surgical site. Bone screw 12 is manipulated including rotation and/or translation for engagement with cortical bone and/or cancellous bone. Receiver 16 is manually engaged with screw shaft 14 in a non-instrumented assembly, as described herein. Bone screw 12 including base 70 having layer 80 enhances fixation and/or facilitates bone growth, as described herein. In some embodiments, tissue becomes imbedded with layer 80 to promote bone growth, enhance fusion of bone screw 12 with vertebral tissue, and/or prevent toggle of bone screw 12 components. In some embodiments, the layer is disposed about at least a portion of an outer circumference of the base.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An implant receiver comprising:
   a body formed by a first manufacturing method, the body extending along a longitudinal axis between opposite proximal and distal end surfaces, the distal end surface extending perpendicular to the longitudinal axis, the body including an outer surface and having spaced-apart walls defining a cavity configured for disposal of a spinal implant, the walls extending parallel to the longitudinal axis, the body defining passageway extending through the distal end surface and parallel to the longitudinal axis; and
   at least one layer being formed onto at least a portion of the outer surface of the body by a second manufacturing method such that the at least one layer defines a portion of the passageway, the at least one layer comprising first and second sections each having a height along the longitudinal axis, the height of the second section being different than the height of the first section, the portion of the outer surface including the distal end surface, the portion of the outer surface being spaced apart from the walls.

2. The implant receiver recited in claim 1, wherein the body has a solid configuration relative to the at least one layer.

3. The implant receiver recited in claim 1, wherein the at least one layer has a porous configuration to promote bone growth through the at least one layer.

4. The implant receiver recited in claim 1, wherein the at least one layer includes a roughened surface to promote bone growth between the implant receiver and bone.

5. The implant receiver recited in claim 1, wherein the body includes a first portion defining the cavity and a second portion including a base, the at least one layer being disposed about at least a portion of an outer circumference of the second portion.

6. The implant receiver recited in claim 1, wherein the at least one layer is disposed about an entire outer circumference of the body.

7. The implant receiver recited in claim 1, wherein the at least one layer is fabricated by additive manufacturing as the second manufacturing method.

8. The implant receiver recited in claim 1, wherein the at least one layer includes a lattice configured to promote bone growth through the at least one layer.

9. The implant receiver recited in claim 1, wherein the at least one layer includes a trabecular configuration.

10. The implant receiver recited in claim 1, wherein the at least a portion of the outer surface of the body provides a fabrication platform for the at least one layer.

11. The implant receiver recited in claim 1, wherein the cavity includes a U-shaped cavity configured for disposal of a spinal rod and the at least a portion of the outer surface includes or is part of a base of the body.

12. A method for fabricating the implant receiver recited in claim 1, the method comprising the steps of:
    forming the body by the first manufacturing method; and
    forming the at least one layer onto the portion of the outer surface by the second manufacturing method, wherein a processor instructs an additive manufacturing apparatus to form the at least one layer.

13. A method as recited in claim 12, wherein the additive manufacturing method includes heating a material in a selective material formation onto the portion of the outer surface.

14. A method as recited in claim 12, wherein the first manufacturing method includes cutting, grinding, rolling, forging, molding, casting, extruding and/or cold working.

15. A method as recited in claim 12, wherein the at least one layer includes a porous layer to promote bone growth through the layer.

16. A method as recited in claim 12, wherein the at least one layer includes a roughened surface to promote bone growth with the body.

17. A method as recited in claim 12, wherein the at least one layer includes a lattice configured to promote bone growth through the at least one layer.

18. A method as recited in claim 12, wherein the at least one layer is disposed about an entire outer circumference of the body.

19. A bone screw comprising:
    a shaft including at least one thread having an external thread form;
    an implant receiver formed by a first manufacturing method, the implant receiver including spaced apart walls defining a U-shaped cavity configured for disposal of a spinal implant and an outer surface, the implant receiver extending along a longitudinal axis between opposite proximal and distal end surfaces, the distal end surface extending perpendicular to the longitudinal axis, the walls extending parallel to the longitudinal axis, the receiver defining passageway extending through the distal end surface and parallel to the longitudinal axis; and a layer formed onto at least a portion of the outer surface by a second manufacturing method such that the layer defines a portion of the passageway, the layer comprising first and second sections each having a height along the longitudinal axis, the height of the second section being less than the height of the first section, the second section being positioned between the walls, the layer comprising a tapered section that connects the first section and the second section, the portion of the outer surface including the distal end surface, the portion of the outer surface being spaced apart from the walls.

20. The bone screw recited in claim 19, wherein the layer is disposed about an entire outer circumference of the implant receiver.

* * * * *